United States Patent [19]

Matsushima et al.

[11] 4,260,831

[45] Apr. 7, 1981

[54] OLIGOMERIZATION OF M-ISOPROPENYLPHENOL

[75] Inventors: Shunsuke Matsushima, Otsu; Kazuhiko Hata, Niihama; Kentaro Mashita, Ibaraki; Shuichi Kanagawa, Osaka; Shinji Nakao, Sakai; Kiyoshi Nakai; Kunimasa Kamio, both of Toyonaka, all of Japan

[73] Assignee: Sumitomo Chemical Company, Limited, Osaka, Japan

[21] Appl. No.: 24,424

[22] Filed: Mar. 27, 1979

[30] Foreign Application Priority Data

Apr. 3, 1978 [JP] Japan .................................. 53-39599
Apr. 4, 1978 [JP] Japan .................................. 53-40090

[51] Int. Cl.³ ............................................ C07C 37/14
[52] U.S. Cl. ..................................... 568/719; 568/720

[58] Field of Search ................................ 568/720, 719

[56] References Cited

FOREIGN PATENT DOCUMENTS 1004168 8/1957 Fed. Rep. of Germany .

*Primary Examiner*—Bernard Helfin
*Attorney, Agent, or Firm*—Stevens, Davis, Miller & Mosher

[57] ABSTRACT m-Isopropenylphenol oligomer which is useful for the production of synthetic resins such as epoxy resins is produced by polymerizing m-isopropenylphenol at a temperature of 135° to 230° C. using a catalytic amount of an acid catalyst in the presence or absence of a solvent, or freezing m-isopropenylphenol in the presence or absence of an acid catalyst.

5 Claims, 4 Drawing Figures

OLIGOMERIZATION OF M-ISOPROPENYLPHENOL

The present invention relates to a process for synthesizing a m-isopropenylphenol oligomer containing the trimer and higher oligomers in addition to the dimer.

p-Isopropenylphenol is already produced on a commercial basis since it is easily obtained from bisphenol A in the presence of an alkali. On the other hand, m-isopropenylphenol has not been obtained in large amounts on a commercial basis because it was only derived from m-hydroxyphenyldimethylcarbinol. Recently, however, m-isopropenylphenol became available as by-product in the commercial production of resorcinol by the oxidation of m-diisopropylbenzene and successive cleavage of the oxidation product. Consequently, studies on the chemical reaction, polymerization and oligomerization of m-isopropenylphenol as monomer are very few, and West German Pat. No. 1,004,168 discloses the synthesis of m-isopropenylphenol dimer. This patent, however, relates to the synthesis of the crystalline dimer of m-isopropenylphenol, not the production of m-isopropenylphenol oligomers containing the trimer and higher oligomers in addition to the dimer.

The inventors have studied to elucidate the oligomerization of m-isopropenylphenol and to find an advantageous process for producing m-isopropenylphenol oligomers on a commercial basis.

As a result, it was found that the oligomers obtained in the present invention are composed of a dimer, trimer, tetramer, pentamer, hexamer, four kinds of substance of unknown structure, and moreover a high molecular weight substance in small amounts, and further that the dimer is present as two isomers. And the isomers were found to have the following chemical formulae which have an indane structure but are different in the position of a phenolic hydroxyl group:

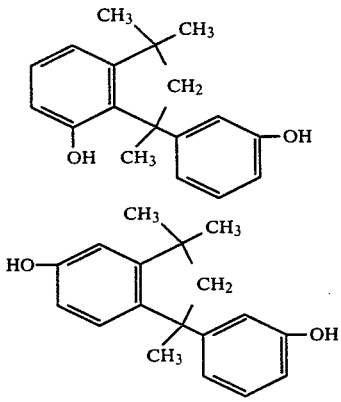

This was found by purifying each of the isomers by subjecting the oligomer mixture to gas-chromatogaphic separation or subjecting the acetylated product of the oligomer mixture to thin-layer chromatographic separation, and examining the structure of each purified isomer by means of infrared spectrum, $H^1$-NMR spectrum and $C^{13}$-NMR spectrum.

In gas-chromatographic determination with a packing having the liquid phase of a non-polar compound, the isomer I is first detected in general because of its shorter retention time and then the peak of the isomer II is recorded (refer to FIG. 1). The presence of the trimer and tetramer was confirmed by the mass spectrum of their acetylated compounds, but components having a larger molecular weight than the tetramer could not be detected by mass spectrum because of their non-volatility.

By liquid-chromatographic determination, the presence of the monomer, dimer, trimer, tetramer, pentamer, hexamer and components considered to have a still larger degree of polymerization was assumed by the peaks recorded at regular intervals (FIG. 2). It was further observed that peaks corresponding to the two kinds of unknown substance followed the aforesaid peaks (FIG. 2).

From the information on infrared spectra, $H^1$-NMR spectrum and $C^{13}$-NMR spectrum, it was assumed that components having a larger molecular weight than the dimer and their isomers have the following chemical structures:

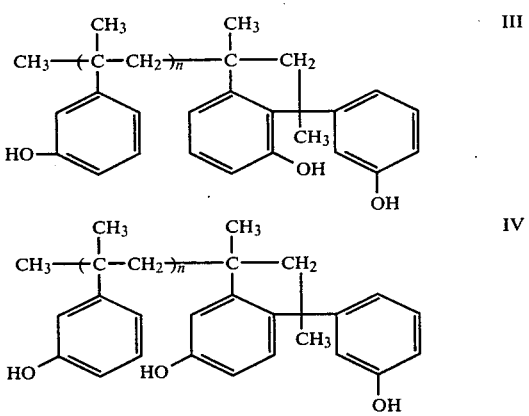

wherein n is 1, 2, 3, 4, etc.

The aforesaid individual oligomers and mixtures of them are useful as materials for the production of synthetic resins. For example, they are used for the modification of epoxy resins, novolak resins, polycarbonate resins, polyester resins and the like.

An object of the present invention is to provide a process for producing an oligomer of m-isopropenylphenol, which comprises (1) polymerizing m-isopropenylphenol at 135° to 230° C. in the presence or absence of a solvent using an acid catalyst, or (2) freezing m-isopropenylphenol in the presence or absence of an acid catalyst.

Figure 1:
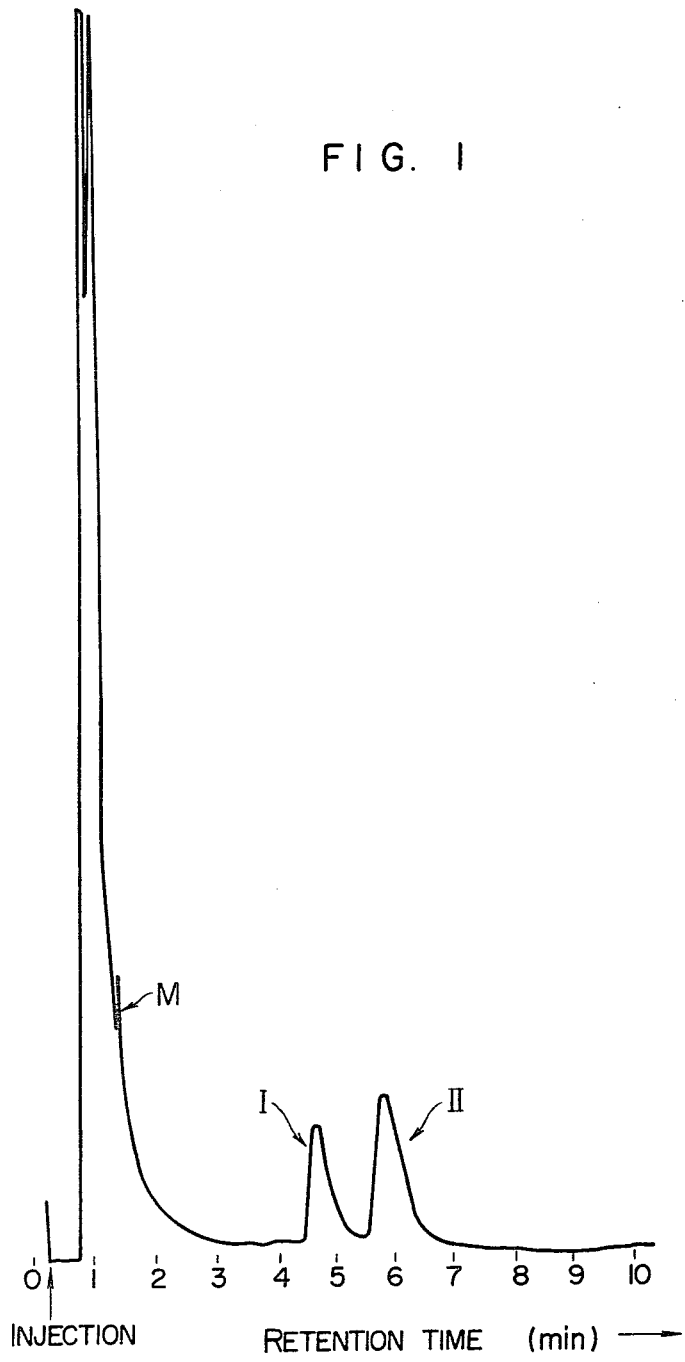
FIG. 1 is one example illustrating the gas-chromatogram of a mixture of m-isopropenylphenol oligomers. In the drawing, M is the peak of the monomer, and I and II show the peaks of the isomeric dimers I and II, respectively.

First, explanation will be given of the process (1). The temperature should be 135° C. or more in order to carry out the present oligomerization substantially rapidly to such a degree that there is little unreacted remaining monomer. When the temperature exceeds 230° C., the produced oligomers begin to decompose and a part of them returns to the original monomer. Consequently, the reaction temperature is 135° to 230° C., preferably 140° to 210° C. By keeping the temperature within this range, reaction systems, particularly of high concentration or containing no solvent, produce the desired oligomer having a low viscosity in a liquid state, so that the reaction operation and removal of reaction heat can be carried out conveniently.

The catalyst used in the process of the present invention includes acid catalysts (e.g. boron trifluoride etherate, boron trifluoride alcoholate, boron trifluoride phenolate, sulfuric acid, phosphoric acid, alkylphosphoric acid, alkylsulfonic acid, alkylbenzenesulfonic acid, naphthalenesulfonic acid, monoalkyl sulfate, aluminum trichloride, iron chloride, etc.), cation exchange resins, activated clay, acid clay, fullers's earth silica-almina, sulfuric acid-treated aluminum hydroxide, solid acid catalysts of the formula $MHSO_4$(M is an alkali metal or ammonium), such as alkali metal bisulfate, and the like. Of these acid catalysts, the solid acid catalysts are preferred from the standpoint of waste water treatment. Further, the solid acid catalysts of the formula, $MHSO_4$ (M is as defined above), have an activity to allow the oligomerization of m-isopropenylphenol to proceed at a proper reaction rate which is neither too fast nor too slow. For example, when the bulk monomer is contacted with this catalyst at 170° to 180° C., 98% of the monomer is converted to the oligomer in about 1 minute. This degree of reaction rate can properly be controlled by elevating and lowering the temperature.

One of the characteristics of this solid acid catalyst is that the pentamer and hexamer are produced in addition to the dimer, trimer and tetramer, while the oligomer produced with other catalysts comprises the latter three components mainly. Consequently, it is naturally expected that the thus obtained oligomer mixture having a high polymerization degree produces epoxy resins and novolak resins which are superior in mechanical strength to those resins produced from oligomer mixtures obtained using the other catalysts.

This solid acid catalyst may be used as a fixed catalyst layer. In this case, almost all of the monomer can be converted to the oligomer as a final product by passing it through the catalyst layer without any solvent. But, the reaction may be stopped at a state wherein a part of the monomer remains unreacted, according to the purposes of use of the final product. The oligomer mixture containing little monomer has a melting point ranging from 50° C. to as high as 80° C., depending upon its composition. This mixture shows a fairly high viscosity at below 135° C., which results in a great loss in pressure when the mixture is passed through the catalyst layer. The viscosity rapidly drops at more than 135° C., for example the viscosity exceeds 1000 cp at 135° C., but is 370 cp at 140° C. and 50 cp at 170° C. In this respect, the oligomerization temperature of the present invention is suitable for the oligomer mixture to pass through the catalyst layer, although the ease of passage depends also upon the particle size of the catalyst.

The amount of the acid catalyst used depends upon both reaction time and reaction temperature, but generally it is within the range of 0.001% to 5% by weight based on the monomer. When the catalyst is used as a fixed catalyst layer, its weight ratio to the monomer can further be decreased because the life of catalyst can be prolonged markedly.

The oligomerization can be carried out without a solvent, when it is carried out at a relatively low temperature, for example at 135° to 160° C., the produced oligomer is so high in viscosity that the use of a little solvent is preferred to allow the reaction to proceed smoothly. When a catalyst of strong activity is used, lowering the rate of reaction by the addition of a solvent is more desirable for the purpose of temperature control. Further, a solvent can also be used for the purpose of changing the composition ratio of oligomers produced.

As suitable solvents used for this reaction, there may be mentioned aromatic hydrocarbons (e.g. benzene, toluene, xylene), aliphatic hydrocarbons (e.g. pentane, hexane, heptane), alicyclic hydrocarbons (e.g. tetralin, decalin, cyclohexane) and halogenated hydrocarbons (e.g. carbon tetrachloride, chloroform, methylene dichloride, monochloromethane, dichloroethane, dichloroethylene, perchloroethylene, bromoform).

When low-boiling compounds are used as a solvent, it is natural to carry out the reaction in a pressure vessel to prevent the boiling thereof.

The amount of the solvent used is within the range of 90% to a very few percent based on the reaction system.

Next, explanation will be given of the process (2).

This process is carried out at a temperature below the melting point of m-isopropenylphenol. Pure m-isopropenylphenol has a melting point of about 20° C., and solid-phase polymerization proceeds below this melting point. m-Isopropenylphenol containing a small amount of impurities has a lower melting point, forming somewhat soft crystals. The solid-phase polymerization proceeds even in such crystals. m-Isopropenylphenol in solution deposits as crystals when it reaches saturation at a low temperature, but the solid-phase polymerization proceeds even in such crystals.

This solid-phase polymerization proceeds relatively slowly during the storage of the crystals, but the rate of polymerization becomes relatively fast when a catalyst is incorporated in the crystals. In order to incorporate the catalyst in the solid crystals, m-isopropenylphenol is once converted to a liquid phase by melting or dissolution in a solvent, a gaseous, liquid or solid catalyst is added to the liquid phase, and then the temperature of the phase is further lowered or the solvent is rapidly evaporated to re-deposit the crystals of m-isopropenylphenol. The solid-phase polymerization can proceed by maintaining this solid state. Further, the polymerization may be promoted by contacting the crystals with the catalyst at the surface.

The solid m-isopropenylphenol containing oligomers which are produced by gradual solid-phase polymerization during the long-term storage of solid, or by rapid solid-phase polymerization promoted by incorporation of the catalyst or contact therewith, is then treated as follows: The unreacted m-isopropenylphenol is separated from the parent solid under reduced pressure at an elevated temperature to obtain a mixture of oligomers.

This separation is also well carried out by a fractional precipitation technique with petroleum ether as a solvent.

The catalyst used for the polymerization (oligomerization) includes boron trifluoride, boron trifluoride etherate, boron trifluoride alcoholate, boron trifluoride phenolate, sulfuric acid, phosphoric acid, alkylphosphoric acid, alkylbenzenesulfonic acid, naphthalenesulfonic acid, monoalkyl sulfate, aluminum trichloride, iron chloride and the like.

The amount of the catalyst used is within a range of 0.01% to 3% by weight based on m-isopropenylphenol.

The catalyst can be removed by washing the reaction product or a solution thereof with a weakly alkaline water or water.

As suitable solvents used for the reaction, there may be mentioned the hydrocarbons and halogenated hydrocarbons used in the process (1). Of these solvents, however, bad solvents which make it easy to preciptitate the crystals at a low temperature, are preferred.

As to the reaction temperature of the solid-phase polymerization, a higher one is preferred because the rate of reaction becomes faster. Generally, however, it is $-120°$ to $20°$ C., $-80°$ C. to $20°$ C., although it depends also upon the reaction conditions.

As to the use of the oligomer mixture obtained by the process of the present invention, using the mixture as it is as a material for the production of synthetic resins is most economical and also desirable in the following point: The broad molecular weight distribution of the oligomer mixture, which contains oligomers of high polymerization degree, is expected as useful for elevating the mechanical strength of epoxy resins and novolak resins.

The oligomer mixture produced by the process of the present invention can be separated into individual pure oligomers. For example, one of the isomers of the dimer can be isolated as crystals from a solution, and the dimer can easily be separated from other oligomers by high-vacuum distillation. Further, oligomers other than the dimer can also be separated into individual oligomers and purified by liquid chromatography using silica gel or alumina as a stationary phase. The separated dimer can be used as a divalent phenol, for example like bisphenol A. The trimer can be used as a branch-forming agent for polycarbonate resins, and oligomers having a further high molecular weight can be used as a strength-improving agent for resins.

The present invention will be illustrated specifically with reference to the following examples, which are not, however, to be interpreted as limiting the invention thereto.

EXAMPLE 1

Seven grams of m-isopropenylphenol was placed in a 25-ml Erlenmeyer flask, and 0.5 g of a cation exchange resin (Dower 50W-X8, produced by Dow Chemical Co.) was added thereto as catalyst. The flask was dipped in an oil bath kept at 140° C. and reaction was carried out for 20 minutes with occasional shaking by hand.

On allowing the reaction solution to stand at room temperature, the whole solution solidified. The colour and melting point of the products and analytical results by liquid-chromatography are as shown in Table 1.

EXAMPLE 2

The procedure was carried out in the same manner as in Example 1 except that the temperature of the oil bath was kept at 170° C. The results are shown in Table 1.

EXAMPLE 3

The procedure was carried out in the same manner as in Example 1 exceptd that the temperature of the oil bath was kept at 200° C. and the reaction time was 5 minutes. The results are shown in Table 1.

EXAMPLE 4

The procedure was carried out in the same manner as in Example 1 except that one drop of conc. sulfuric acid was added as catalyst, the temperature of the oil bath was kept at 170° C., and that the reaction time was 5 minutes. The results are shown in Table 1.

EXAMPLE 5

The procedure was carried out in the same manner as in Example 1 except that 0.5 g of activated clay powder was added as catalyst, the temperature was kept at 170° C., and that the reaction time was 5 minutes. The results are shown in Table 1.

Reference example

The procedure was carried out in the same manner as in Example 1 except that 0.5 g of activated clay powder was added as catalyst, the temperature was kept at 90° C., and that the reaction time was 2 hours. The results are known in Table 1.

EXAMPLE 6

The procedure was carried out in the same manner as in Example 1 except that 0.5 g of acid clay powder was added as catalyst, the temperature was kept at 170° C., and the reaction time was 5 minutes. The results are shown in Table 1.

EXAMPLE 7

The procedure was carried out in the same manner as in Example 1 except that 0.5 g of sodium bisulfate monohydrate powder (NaHSO$_4$.H$_2$O) was added as catalyst, the temperature was kept at 170° C., and that the reaction time was 5 mintures. The results are shown in Table 1.

EXAMPLE 8

The procedure was carried out in the same manner as in Example 1 except that 0.5 g of lithium bisulfate powder (LiHSO$_4$) was added as catalyst, the temperature was kept as 150° C. and that the reaction time was 5 minutes. The results are shown in Table 1.

EXAMPLE 9

The procedure was carried out in the same manner as in Example 1 except that 15 ml of a decalin solution containing 15% of m-isopropenylphenol was used in place of 7 g of m-isopropenylphenol, 0.5 g of potassium bisulfate powder (KHSO$_4$) was added as catalyst, the temperature was kept at 160° C., and that the reaction time was 2 hours. On allowing the reaction solution to stand at room temperature, the reaction product deposited to the bottom and solidified. This solidified portion was analyzed. The results are shown in Table 1.

EXAMPLE 10

Activated clay powder was shaped into tablets by a tablet-making machine, powdered and passed through a sieve to collect coarse particles of about 0.5 mm in diameter. Thereafter, 0.7 g of the particles was packed in a glass reactor tube of 4 mm in diameter, and the catalyst layer in the tube was fixed at both ends with glass wool. The glass reactor tube was then heated to 170° C. from the outside, and 20 g of molten m-isopropenylphenol was passed through the catalyst layer by sa pump at rate of 0.2 ml/min. The reaction solution coming out of the catalyst layer solidified. The results are shown in Table 1.

EXAMPLE 11

1.5 Gram of commercially available potassium bisulfate powder ($KHSO_4$) was packed as it is in the same glass reactor tube as in Example 10, and the catalyst layer was fixed at both ends with glass wool. The tube was then heated to 170° C. from the outside, and 220 g of molten m-isopropenylphenol was passed through the catalyst layer by a pump at a rate of 0.2 ml/min. The reaction solution coming out of the tube was separately collected at every 20 g of fraction and numbered, 1, 2, 3, ..., 11.

Figure 2:
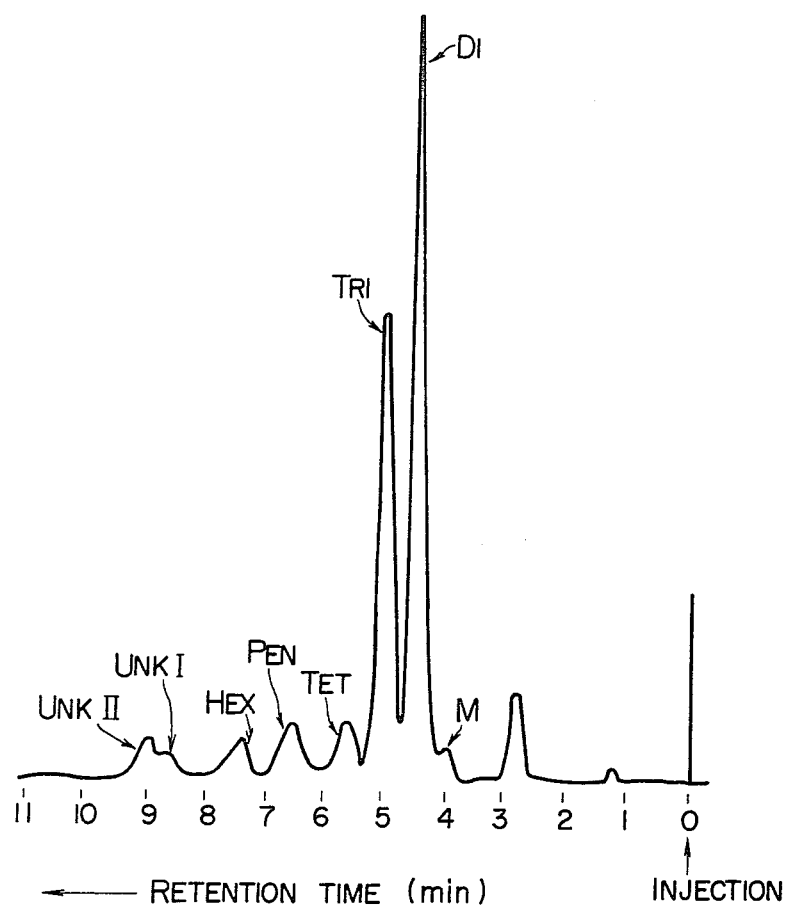
FIG. 2 is the chromatogram obtained by subjecting the mixture of m-iso-propenylphenol oligomers of the fraction No. 6 obtained in Example 11 to liquid-chromatography. In the drawing, M, Di, Tri, Tet, Pen, Hex, Unk I and Unk II show the peaks of monomer, dimer, trimer, tetramer, pentamer, hexamer, unknown substance I and unknown II, respectively.

On standing, every fraction solidified in a short time. The fractions, Nos. 1, 2 and 3, were a deep brown solid, but the fraction No. 4 became paler and the fractions, No. 6 and thereafter, were a pale red solid. These solids crystallized on standing at room temperature, and cracks appeared throughout almost the whole solid. The analytical results of the typical fractions, Nos. 1, 6 and 11, are shown in Table 1. The liquid-chromatogram of the fraction No. 6 is shown in FIG. 2.

TABLE 1

| | Reaction Conditions | | | | Composition of product (%) | | | | | | | | | State of product | |
|---|---|---|---|---|---|---|---|---|---|---|---|---|---|---|---|
| | Catalyst | | Reaction temperature (°C.) | Reaction time | Monomer | Dimer | Trimer | Tetramer | Pentamer | Hexamer | Unknown substance I | Unknown substance II | Unknown substance III | Color | Melting point (°C.) |
| Example | Kind | Weight (g) | | | | | | | | | | | | | |
| 1 (1) | Ion-exchange resin | 0.5 | 140 | 20 min | 1.7 | 57.0 | 27.5 | 3.7 | 3.2 | 2.9 | — | — | 4.1 | Pale red | 54 |
| 2 (1) | Ion-exchange resin | 0.5 | 170 | 20 min | 0.8 | 47.5 | 34.4 | 5.3 | 3.7 | 2.7 | — | 1.2 | 4.5 | Pale red | 57 |
| 3 (1) | Ion-exchange resin | 0.5 | 200 | 5 min | 3.8 | 48.0 | 32.1 | 6.1 | 3.0 | 3.0 | — | 1.0 | 3.1 | Pale red | 50 |
| 4 (1) | Sulfuric acid | 0.1 | 170 | 5 min | 2.6 | 50.0 | 40.0 | 1.4 | — | — | — | — | 6.0 | Deep brown | 58 |
| 5 (1) | Activated clay | 0.5 | 170 | 5 min | 1.9 | 59.8 | 30.5 | 2.5 | 0.3 | 0.3 | — | — | 5.3 | Pale brown | 63 |
| Reference example (1) | Activated clay | 0.5 | 90 | 2 hr | 5.2 | 64.3 | 26.9 | 0.8 | 0.4 | 0.4 | — | — | 2.0 | Pale brown | 61 |
| 6 (1) | Acid clay | 0.5 | 170 | 5 min | 1.8 | 63.5 | 28.1 | 4.4 | — | — | — | — | 3.2 | Pale brown | 59 |
| 7 (1) | $NaHSO_4 \cdot H_2O$ | 0.5 | 170 | 5 min | 2.5 | 47.1 | 27.4 | 6.6 | 4.8 | 3.4 | — | 0.8 | 3.2 | Pale yellow | 63 |
| 8 (1) | $LiHSO_4$ | 0.5 | 150 | 5 min | 3.0 | 54.5 | 26.1 | 6.3 | 3.5 | 3.1 | — | 0.4 | 3.1 | Pale yellow | 62 |
| 9 (2) | $KHSO_4$ | 0.5 | 160 | 2 hr | 1.9 | 38.2 | 31.9 | 7.2 | 7.5 | 6.5 | — | 2.9 | 2.6 | Pale red | 65 |
| 10 (3) | Activated clay | 0.7 | 170 | 0.2 g/min* | 52.0 | 29.3 | 14.1 | 2.0 | — | — | — | — | 2.6 | Pale yellow | 50 |
| 11 No. 1 (3) | $KHSO_4$ | 1.5 | 170 | 0.2 g/min* | 3.1 | 48.6 | 27.4 | 4.4 | 6.4 | 4.0 | — | 1.4 | 4.7 | Deep brown | 58 |
| 11 No. 6 (3) | $KHSO_4$ | 1.5 | 170 | 0.2 g/min* | 1.9 | 47.3 | 30.2 | 5.4 | 5.1 | 4.0 | — | 1.1 | 5.1 | Pale red | 60 |
| 11 No. 11 (3) | $KHSO_4$ | 1.5 | 170 | 0.2 g/min* | 1.5 | 50.1 | 28.8 | 4.4 | 5.1 | 3.0 | — | 1.3 | 4.9 | Pale red | 71 |

Note:
(1) Seven grams of m-isopropenylphenol was used.
(2) Fifteen milliliters of a 15% m-isopropenylphenol solution in decalin was used.
(3) Continuous reaction
*Feed rate of m-isopropenylphenol

EXAMPLE 12

Figure 3:
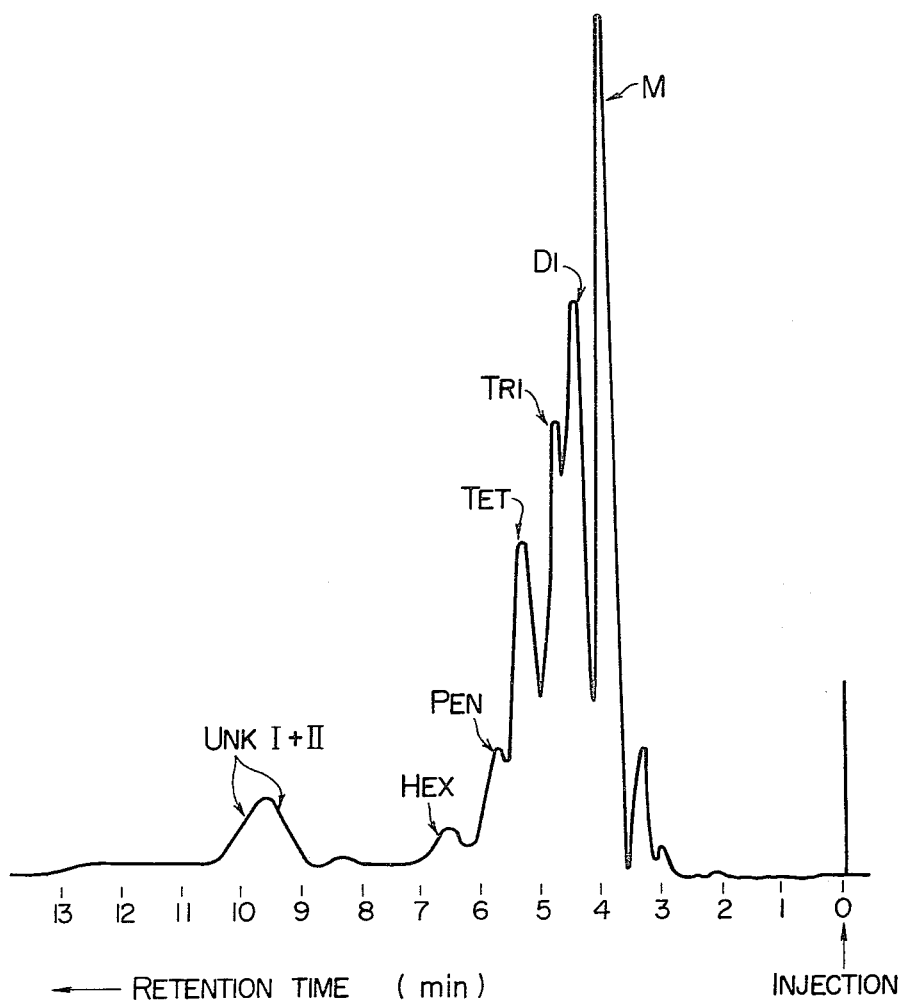
FIG. 3 is the liquid-chromatogram of the oligomer mixture obtained in Example 12. In the drawing, M, Di, Tri, Tet, Pen, Hex and Unk IV show the peaks of monomer, dimer, trimer, tetramer, pentamer, hexamer and unknown substance IV, respectively.
Figure 4:
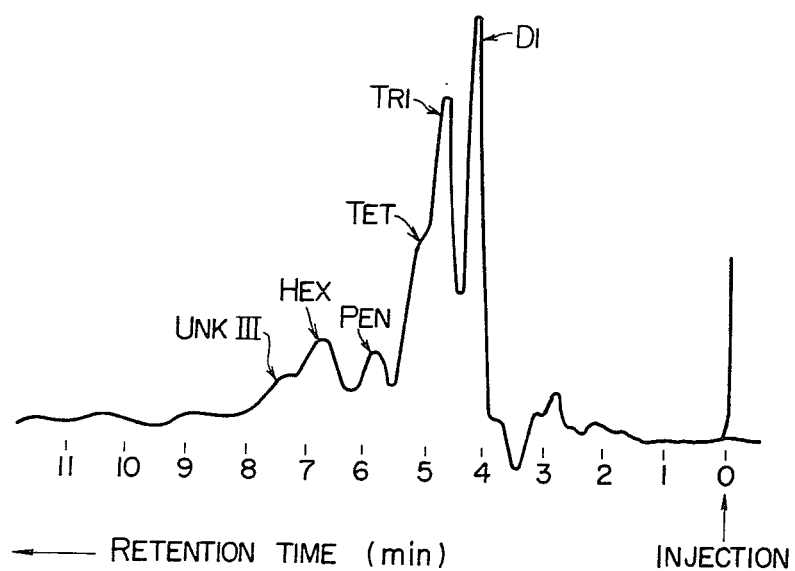
FIG. 4 is the liquid-chromatogram of the oligomer mixture obtained in Example 13. In the drawing, the peaks are the same as in FIG. 3, provided that Unk III shows the peak of unknown substance III.

Seventy grams of crystalline m-isopropenylphenol was kept at −20° C. for about 9 months was distilled under reduced pressure to separate m-isopropenylphenol as a fraction at 124° C. under 7 mmHg and to obtain 8.2 g of a resinous pale yellow solid as a residual matter. The solid was analyzed by liquid-chromatography (FIG. 3). The results are shown in Table 2.

EXAMPLE 13

134.2 Grams of m-isopropenylphenol was dissolved in 337 ml of toluene, and 2.9 g of boron trifluoride ethyl etherate ($BF_3 \cdot OEt_2$) was added thereto. The mixture was immediately cooled to −50° C. and allowed to stand for 6 hours. Thereafter, the whole reaction mass was poured into a 2 liters of petroleum ether to precipitate the produced oligomers. The precipitate was dried at 50° C. under 10 mmHg to obtain 102.3 g of a pale brown solid. The solid was analyzed by liquid-chromatography. The results are shown in Table 2.

TABLE 2

| Example | Monomer | Dimer | Trimer | Tetramer | Pentamer | Hexamer | Unknown substance III | Unknown substance IV |
|---|---|---|---|---|---|---|---|---|
| 12 | 27 | 24 | 17 | 17 | 6 | 2 | 7 | 0 |
| 13 | 1 | 28 | 31 | 13 | 8 | 13 | 0 | 6 |

What is claimed is:

1. A process for producing a mixture of m-isopropenylphenol oligomers comprising dimers, trimers and higher oligomers which comprises polymerizing m-isopropenylphenol at a temperature of 140° to 210° C. using a catalytic amount of an acid catalyst selected from the group consisting of boron trifluoride etherate, boron trifluoride alcoholate, boron trifluoride phenolate, sulfuric acid, phosphoric acid, alkylphosphoric acid, alkylsulfonic acid, alkylbenzenesulfonic acid, naphthalenesulfonic acid, monoalkylsulfate, aluminum trichloride, iron chloride, cation exchange resins, activated clay, acid clay, fuller's earth, silicaalumina, sulfuric acid-treated aluminum hydroxide and alkali metal bisulfates of the formula, $MHSO_4$, wherein M is an alkali metal or ammonium, in the presence or absence of a small amount of a hydrocarbon or halogenated hydrocarbon solvent.

2. The process acoording to claim 1, wherein the acid catalyst is one member selected from solid acid catalysts.

3. The process according to claim 2, wherein the solid acid catalyst is one member selected from the solid acid catalysts of the formula, $MHSO_4$, wherein M is an alkali metal or ammonium.

4. The process according to claim 1, wherein the polymerization is effected by passing m-isopropenylphenol through a fixed acid catalyst layer.

5. The process according to claim 1, wherein the solvent is one member selected from aromatic hydrocarbons, aliphatic hydrocarbons, alicyclic hydrocarbons and halogenated hydrocarbons.

* * * * *